(12) United States Patent
Hudson et al.

(10) Patent No.: US 10,617,397 B2
(45) Date of Patent: Apr. 14, 2020

(54) SAMPLE CAPTURE AND TRANSPORT UNIT

(71) Applicant: INTELLIGENT FINGERPRINTING LIMITED, Cambridge, Cambridgeshire (GB)

(72) Inventors: Mark Hudson, Norwich (GB); Nicholas Earl, Cambridge (GB); Daniel Peterson Godfrey, Cambridge (GB); John Dunton, Cambridge (GB)

(73) Assignee: INTELLIGENT FINGERPRINTING LIMITED, Cambridge (GB)

( * ) Notice: Subject to any disclaimer, the term of this patent is extended or adjusted under 35 U.S.C. 154(b) by 512 days.

(21) Appl. No.: 14/915,138

(22) PCT Filed: Aug. 22, 2014

(86) PCT No.: PCT/GB2014/052579
§ 371 (c)(1),
(2) Date: Feb. 26, 2016

(87) PCT Pub. No.: WO2015/028785
PCT Pub. Date: Mar. 5, 2015

(65) Prior Publication Data
US 2016/0199044 A1    Jul. 14, 2016

(30) Foreign Application Priority Data

Aug. 30, 2013   (GB) .................................. 1315444.8

(51) Int. Cl.
*A61B 10/00*        (2006.01)
*A61B 10/02*        (2006.01)
(Continued)

(52) U.S. Cl.
CPC ........ *A61B 10/0096* (2013.01); *A61B 5/1172* (2013.01); *A61B 5/14517* (2013.01);
(Continued)

(58) Field of Classification Search
CPC .................................................. A61B 10/0096
See application file for complete search history.

(56) References Cited

U.S. PATENT DOCUMENTS

| | | |
|---|---|---|
| 4,430,299 A | 2/1984 | Horne |
| 2004/0126281 A1 | 7/2004 | Morrison |

(Continued)

FOREIGN PATENT DOCUMENTS

| | | |
|---|---|---|
| CN | 1164076 A | 11/1997 |
| CN | 2686534 Y | 3/2005 |

(Continued)

OTHER PUBLICATIONS

International Search Report and Written Opinion dated Oct. 23, 2014 from corresponding PCT Application No. PCT/GB2014/052579.

(Continued)

*Primary Examiner* — Daniel L Cerioni
*Assistant Examiner* — Yasmeen S Warsi
(74) *Attorney, Agent, or Firm* — Lando & Anastasi, LLP (57) ABSTRACT

A sample capture and transport unit comprises a housing defining a substrate chamber for containing a sample-capture substrate. The housing comprises at least a first part and a second part which are movable relative to one another • i) from a first closed configuration in which the substrate chamber is inaccessible; • ii) to a first open configuration in which access to the substrate chamber is enabled to allow capturing of a skin-print on a sample-capture substrate contained within the substrate chamber; and subsequently • iii) into a second closed configuration in which the substrate chamber is again inaccessible. The unit further comprises a retaining mechanism for retaining it in the second closed configuration. The retaining mechanism is disablable to permit movement of the unit out of the second closed (Continued)

configuration. A sample can be obtained at a first location, secured for transport and analysed at a second location.

23 Claims, 6 Drawing Sheets

(51) Int. Cl.
*A61B 5/1172* (2016.01)
*B01L 3/00* (2006.01)
*A61B 5/145* (2006.01)
*A61B 5/00* (2006.01)

(52) U.S. Cl.
CPC .............. *A61B 10/02* (2013.01); *B01L 3/508* (2013.01); *A61B 5/4845* (2013.01); *A61B 10/0064* (2013.01); *A61B 2560/0406* (2013.01); *A61B 2560/0431* (2013.01); *B01L 2200/141* (2013.01); *B01L 2300/045* (2013.01); *B01L 2300/0654* (2013.01)

(56) References Cited

U.S. PATENT DOCUMENTS

| | | |
|---|---|---|
| 2005/0158725 A1 | 7/2005 | Yukimasa et al. |
| 2010/0079046 A1 | 4/2010 | Vint |
| 2011/0304001 A1* | 12/2011 | Erhart ................ G06K 9/00053 257/433 |

FOREIGN PATENT DOCUMENTS

| | | |
|---|---|---|
| CN | 203138498 U | 8/2013 |
| EP | 2574399 A1 | 4/2013 |
| GB | 2228231 A | 8/1990 |
| JP | H4123462 U | 11/1992 |
| JP | 2003196646 A | 7/2003 |
| JP | 2004306962 A | 11/2004 |
| JP | 2009207726 A | 9/2009 |
| WO | 2006115499 A1 | 11/2006 |
| WO | 2010109445 A1 | 9/2010 |
| WO | 2013045587 A1 | 4/2013 |

OTHER PUBLICATIONS

Written Opinion of the International Preliminary Examining Authority dated Aug. 3, 2015 from corresponding PCT Application No. PCT/GB2014/052579.

International Preliminary Report on Patentability dated Nov. 23, 2015 from corresponding PCT Application No. PCT/GB2014/052579.

Combined Search and Examination Report dated Feb. 24, 2014 from corresponding GB Patent Application Serial No. 1315444.8.

* cited by examiner

SAMPLE CAPTURE AND TRANSPORT UNIT

CROSS-REFERENCE TO RELATED APPLICATIONS

This application is a U.S. national phase application and claims the benefit of priority under 35 U.S.C. § 371 of PCT/GB2014/052579, titled SAMPLE CAPTURE AND TRANSPORT UNIT and filed on Aug. 22, 2014, which in turn claims priority to GB1315444.8 filed on Aug. 30, 2013, the contents of both of which are hereby incorporated herein by reference in their entireties for all purposes.

BACKGROUND

An impression left by the friction ridges of human skin, such as the skin of a human finger contains information regarding the identity of the human. It is widely known that the appearance of the impression of the human finger, known as a fingerprint, is unique to each human and may be used to confirm the identity of the human. The appearance of the impression of the skin of other human body parts may also be unique to each human and so may also be used to confirm the identity of the human. Such impressions of human skin, when not specific to the skin of the human finger, may be called skin-prints.

In addition to the appearance of the impression left by human skin, the impression may contain chemical species which themselves may be detected in order to obtain further information.

For example, when a human intakes a substance (e.g. by ingestion, inhalation or injection) the substance may be metabolised by the human body giving rise to secondary substances known as metabolites. The presence of a particular metabolite can be indicative of a specific intake substance. The intake substance and/or metabolites may be present in sweat and, as such, may be left behind in the skin-print, e.g. a fingerprint. Detection of such metabolites in a skin-print can be used as a non-invasive method of testing for recent lifestyle activity such as (but not limited to) drug use, or compliance with a pharmaceutical or therapeutic treatment regime.

Importantly, the taking of a skin-print is much simpler than obtaining other body fluids such as blood, saliva and urine, and is more feasible in a wider range of situations. Not only this but since the appearance of the skin-print itself provides confirmation of the identity of the person providing the skin-print, there can be greater certainty that the substance or substances in the skin-print are associated with the individual. This is because substitution of a skin-print, particularly a fingerprint, is immediately identifiable from appearance whereas substitution of, for example, urine, is not immediately identifiable from appearance. As such, testing for one or more substances in a skin-print provides a direct link between the one or more substances and the identity of the human providing the skin-print.

It is important, therefore, that a substrate on which a skin-print is collected cannot be contaminated (either innocently or maliciously) before or after the impression of the skin is taken. The substrate must be accessible only for the short period during which the skin-print is taken and then not again until the skin-print impression is analysed under strictly controlled conditions which avoid contamination.

STATEMENTS OF INVENTION

Against this background, there is provided a sample capture and transport unit, comprising a housing defining a substrate chamber for containing a sample-capture substrate, the housing comprising at least a first part and a second part which are movable relative to one another
  i) from a first closed configuration in which the substrate chamber is inaccessible;
  ii) to a first open configuration in which access to the substrate chamber is enabled to allow capturing of a skin-print on a sample-capture substrate contained within the substrate chamber; and subsequently
  iii) into a second closed configuration in which the substrate chamber is again inaccessible;

wherein the sample capture and transport unit further comprises a retaining mechanism for retaining the sample capture and transport unit in the second closed configuration wherein the retaining mechanism is disablable to permit movement of the sample capture and transport unit out of the second closed configuration.

The substrate may be of a material suitable for the analysis which is to be carried out on the sample. The substrate may be planar. The substrate may be opaque or transparent depending on the technique of analysis and/or imaging to be used. The substrate may have marks printed, moulded or etched on to a surface of the substrate to indicate where the sample is to be placed. The substrate may be permanently installed in the housing or may, in limited circumstances, be releasable from the housing for the purpose of analysis, for example by releasing clips.

The retaining mechanism may take a variety of forms. For example, it may comprise purely mechanical components, it may comprise one or more electromechanical components, such as an electromagnet, it may comprise a lock or it may comprise a number of further alternatives.

In this way, the sample capture and transport unit may effectively be prevented from being released from the second closed position, either accidentally or maliciously, until the retaining mechanism is disabled.

That the retaining mechanism is disablable means that the retaining mechanism can be disabled in order that first and second parts of the sample capture and transport unit can be moved relative to one another so as to move out of the second closed configuration. Without disabling the retaining mechanism the sample capture and transport unit is prevented from moving out of the second closed configuration.

In the case of a retaining mechanism comprising only mechanical components, disabling the retaining mechanism may, for example, involve movement of one component with respect to another such as releasing one from another. In the case of a lock, disabling may involve unlocking with a key, which may or may not be of a conventional key form. In the case of a retaining mechanism with one or more electromechanical components, it may comprise sending of a signal and/or changing a voltage level to release, for example, an electromagnet. Disabling the retaining mechanism may include, instead of or in addition to any of the above, damaging or breaking the retaining mechanism so that it is no longer functional and such that first and second parts of the housing can be moved relative to one another so as to move out of the second closed configuration.

Consequently, it is possible to obtain a sample at a first location, secure the sample in such a manner that subsequent access to the sample is prevented until being released, wherein the releasing may take place at a second location and analyse the sample at the second location. This has the advantage of providing the possibility of a secure evidential trail that the sample has not been accessed (and therefore not contaminated) between being obtained and being analysed.

Further, it has the advantage of providing the possibility of a secure evidential trail that the substrate has not been accessed (and therefore not contaminated) prior to receipt of a skin-print.

The sample capture and transport unit may further comprise a tamper evident feature wherein access to the retaining mechanism for disabling the retaining mechanism is available only by triggering the tamper evident feature.

The tamper evident feature may take a variety of forms. It may comprise a frangible element such as a perforated component, a pull tab, a piercable component or any other feature which prevents access other than by breaking, removing or otherwise irreversibly altering or damaging the tamper evident feature so as to be immediately clear, visually or otherwise, that the tamper evident feature has been triggered. It may, alternatively or in addition, comprise one or more electronic tamper evident components. For example, the tamper evident feature may comprise one or more sensors and one or more electronic output devices such that when the tamper evident feature is triggered, one or more of the electronic output is altered. In one specific example, this may be switching on or off of one or more LEDs. For example, an LED of a first colour may be configured to emit light of the first colour in the event that the tamper evident feature has not been triggered and an LED of a second colour may be configured to emit light of the second colour in the event that the tamper evident feature is triggered. In an alternative, an LED may be configured to emit light only in the event of triggering of the tamper evident feature. The skilled person will recognise multiple further possible arrangements of LED to communicate whether or not a the tamper evident feature has been triggered.

In further alternatives, the tamper evident feature may comprise an RF tag which may be triggered by moving the sample capture and transport unit out of the second closed position such that if the tag is already activated before the time of intended analysis then it is clear that the transport unit has already been moved out of the second closed position and may therefore have been contaminated.

In a further alternative, the tamper evident feature may be of the sort which, when triggered, releases a permanent substance such as an indelible ink or a chemical marker which would be immediately determinable on analysing (for example by optical or chemical analysis) a substrate within the sample capture and transport unit.

The tamper evident feature may be any feature which indicates that the sample capture and transport unit has been moved out of the second closed position. The means of this indication may be directly visible to a human or otherwise detectable.

It may be that access to the retaining mechanism for disabling the retaining mechanism is restricted.

Such a restriction may, for example, comprise an aperture configured to be passed straightforwardly by a correspondingly specifically configured component but which would otherwise be awkward to access.

The sample capture and transport unit may further comprise a non-return feature which prevents movement from the first open configuration to the first closed configuration.

Such a non-return feature may comprise one or more mechanical components and/or one or more electromechanical components, optionally in combination with control electronics.

The sample capture and transport unit may further comprise a second open configuration accessible only by disabling the retaining mechanism.

In a further aspect, the invention comprises a machine for analysing a sample received on a sample-capture substrate located in a substrate chamber of the sample capture and transport unit, the machine comprising:

means for engaging with the sample capture and transport unit in order to disable or damage the retaining element which prevents movement from the first open configuration to the first closed configuration.

Where the sample capture and transport unit comprises a tamper evident feature, the machine may comprise means to check whether the tamper evident feature has been triggered. Further, the machine may reject any sample capture and transport unit having a tamper evident feature that has been triggered.

In a further aspect, the invention comprises a method of obtaining a sample at a first location, securing the sample for transport and analysing the sample at a second location using the sample capture and transport unit and a sample-capture substrate contained therein, the method comprising the following steps:

at the first location, moving the sample capture and transport unit from the first closed configuration to the first open configuration;

receiving a sample on the sample-capture substrate located in the substrate chamber;

moving the sample capture and transport unit from the first open configuration to the second closed configuration; and disabling the retaining mechanism in order to access the sample-capture substrate for analysis.

In this way, it is possible to retain the sample capture and transport unit in the second closed configuration once a sample has been received onto the substrate and then transport the sample capture and transport unit to a second location before disabling the retaining mechanism in order to access the sample-capture substrate for analysis.

While these aspects of the invention are particularly appropriate to fingerprints, they may be used in relation to any skin-prints such as, but not limited to, ear prints, toe prints and palm prints. Moreover, the sample capture and transport unit may be used for receiving samples other than skin-prints. For example, sweat may be applied to the substrate via a swab rather than directly via a fingerprint. Other bodily fluids and other types of sample may similarly be applied to the substrate.

BRIEF DESCRIPTION OF THE FIGURES

A specific embodiment of the invention will now be described, by way of example only, with reference to the accompanying drawings in which.

SPECIFIC DESCRIPTION

In a first embodiment, the sample capture and transport unit 1 comprises a transparent substrate, optionally of glass. The substrate comprises a front surface for receiving a skin-print and a rear surface opposite the front surface.

Figure 6:
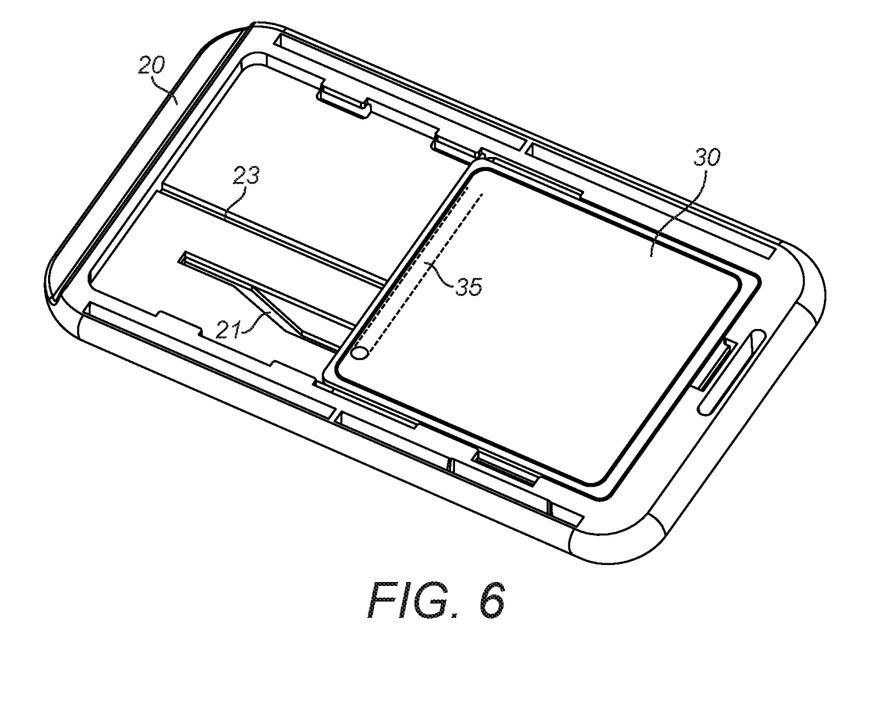
FIG. 6 shows a rear view of the first embodiment of the sample capture and storage unit.

The substrate is enclosed within a housing 2 and retained within the housing 2 by retaining clips. The housing 2 acts to protect the substrate except when it is necessary for it to be exposed (in particular, for receiving a skin-print and for analysis). The housing may be opaque in order to protect substances that are susceptible to photodegradation which may be present on the substrate. The housing 2 comprises a frame 20 with a substrate receiving portion 26, best shown in FIG. 2. The housing 2 also comprises a front shutter 10 (best shown in FIG. 1) and a rear shutter 30 (best shown in FIG. 6). The front shutter 10 comprises an inside 10a that faces inwardly towards the substrate and an outside 10b which faces outwardly. The front shutter 10 may further comprise a thumb grip 18 on the outside 10b of the front shutter. The rear shutter 30 comprises an inside 30a that faces inwardly towards the substrate and an outside 30b which faces outwardly.

The front shutter 10 is movable with respect to the frame 20 from a first closed position (shown in FIG. 1) in which the front surface of the substrate is covered by the front shutter 10 to a first open position in which the front surface of the substrate is exposed, in particular for receipt of a skin-print.

Figure 1:
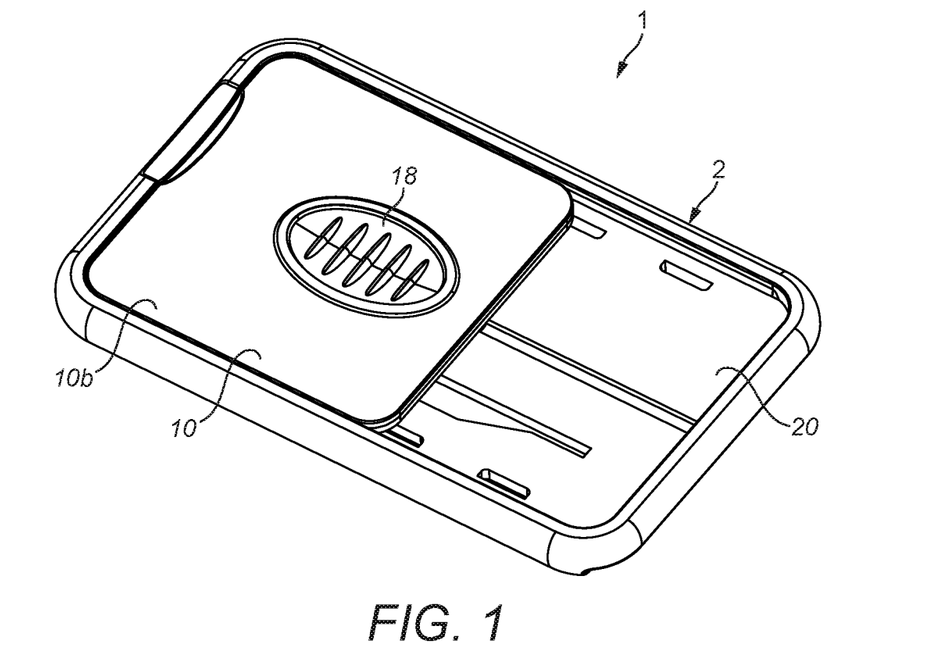
FIG. 1 shows a front view of sample capture and storage unit in accordance with a first embodiment of the invention.
Figure 2:
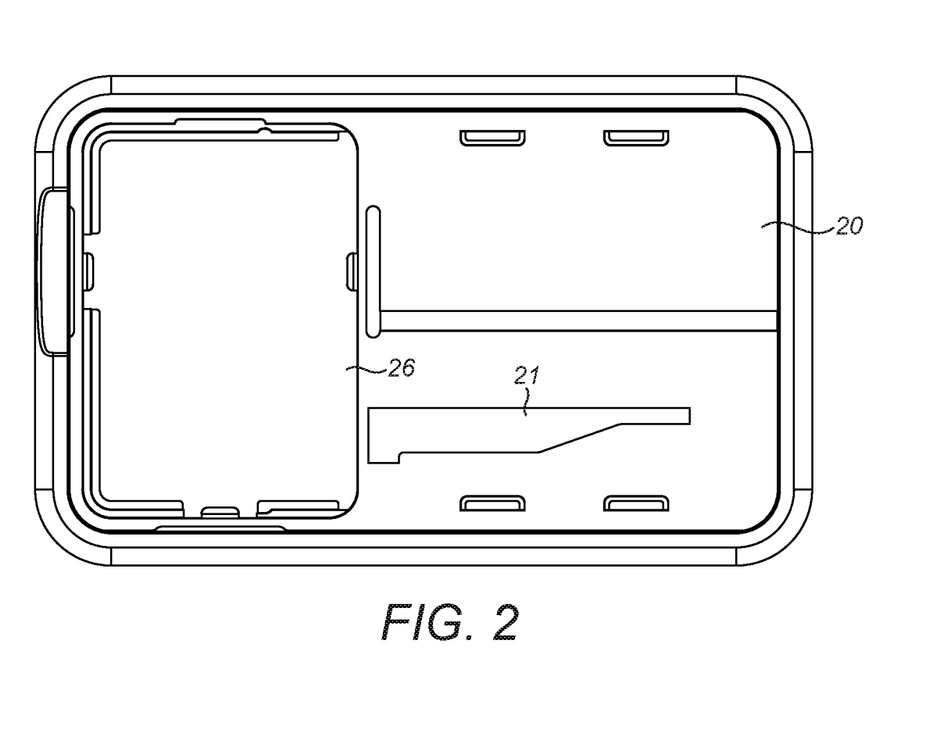
FIG. 2 shows a top side of a frame of the sample capture and storage unit of the first embodiment of the sample capture and storage unit.

The front shutter 10 is also movable with respect to the frame 20 from the first open position to a second closed position in which the front surface of the substrate is covered by the front shutter 10.

Figure 4:
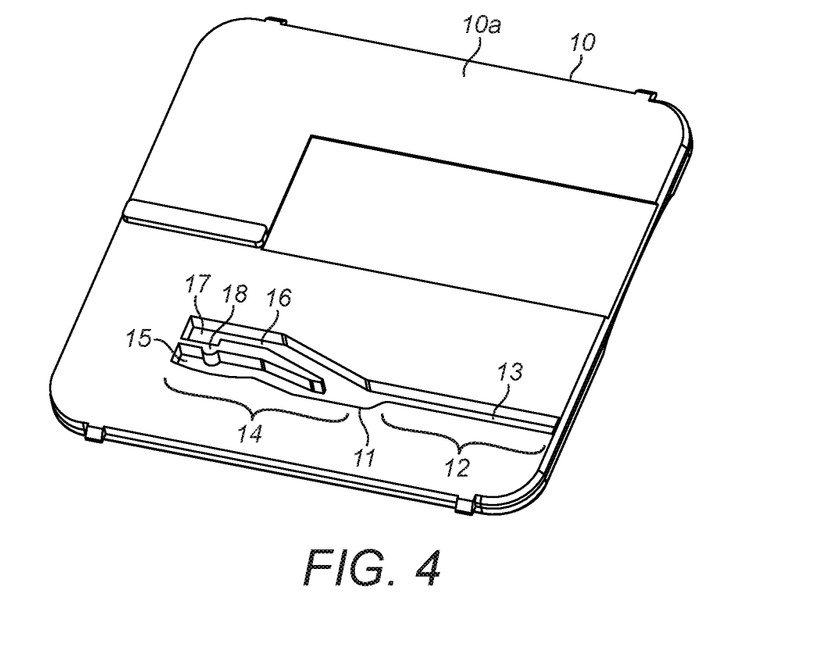
FIG. 4 shows an inside of the front shutter of the first embodiment of the sample capture and storage unit.
Figure 5:
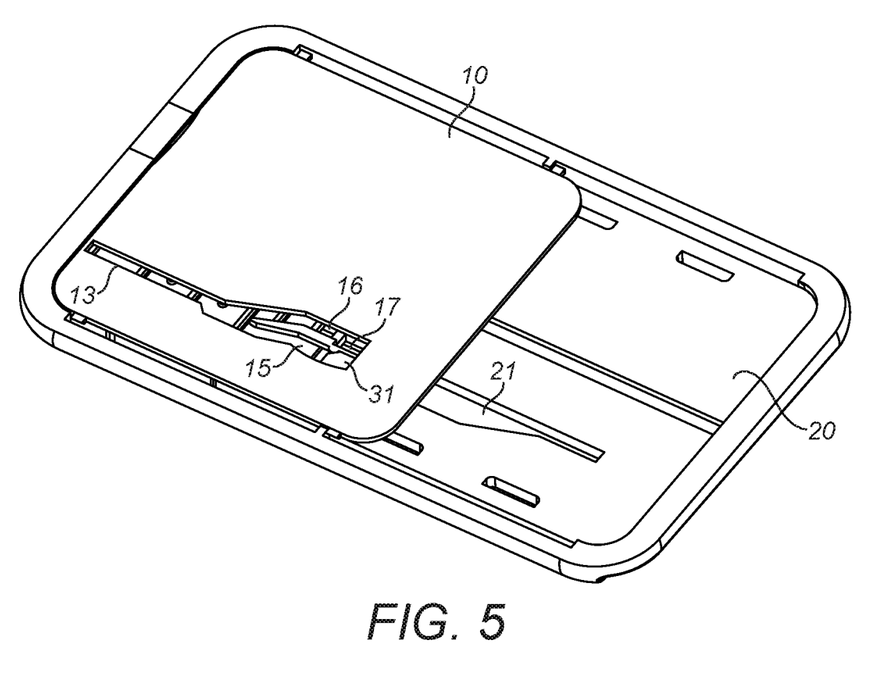
FIG. 5 shows a section through the front shutter of FIGS. 3 and 4 in situ of the first embodiment of the sample capture and storage unit.

The inside 10a of the front shutter 10 comprises a bifurcated channel arrangement 11, best seen in FIG. 4. The bifurcated channel arrangement 11 comprises a first part 12 comprising a common channel 13 and a second part 14 comprising a primary channel 15 and a secondary channel 16, the primary channel 15 and the secondary channel 16 being substantially parallel. The primary channel comprises a protrusion 18 and the secondary channel comprises a first detent 17.

Figure 7:
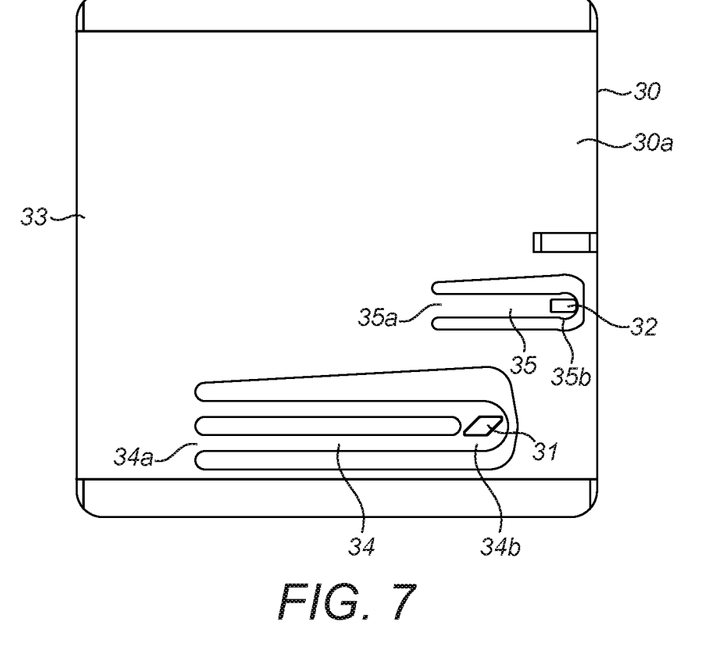
FIG. 7 shows an inside view of a rear shutter of the first embodiment of the sample capture and storage unit.
Figure 8:
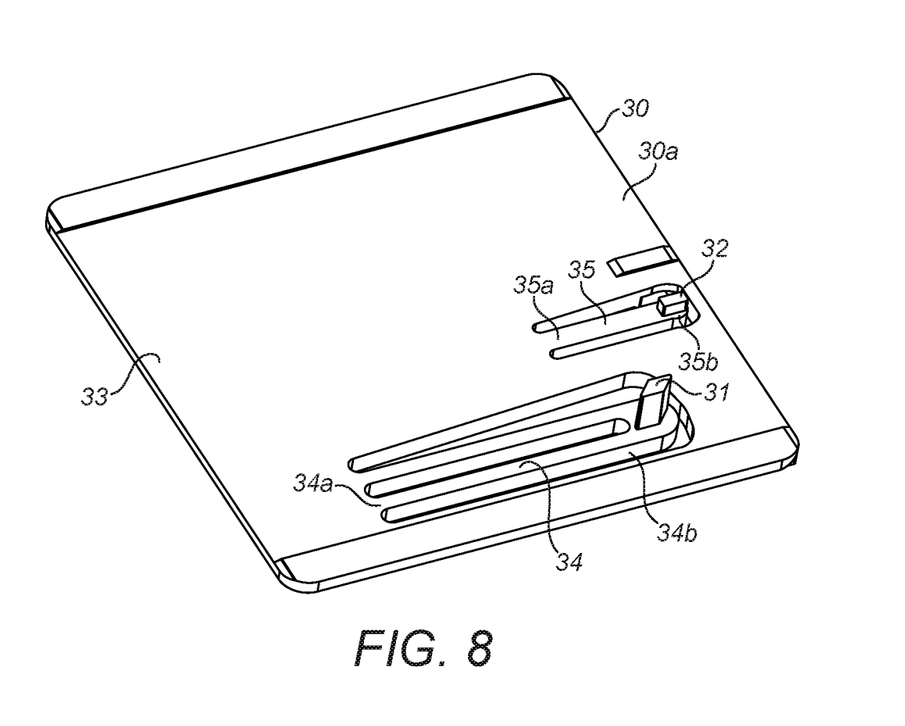
FIG. 8 shows a perspective inside view of a rear shutter of the first embodiment of the sample capture and storage unit.
Figure 9:
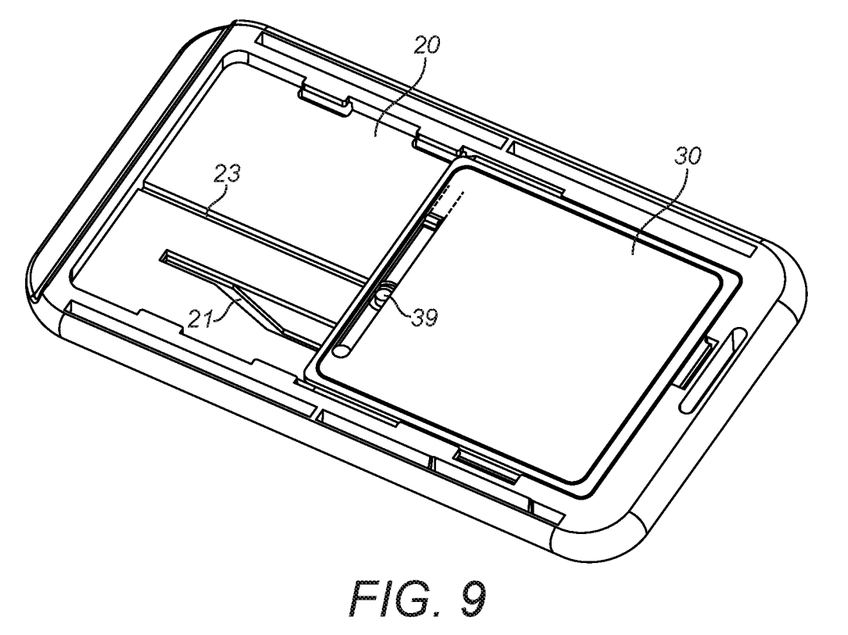
FIG. 9 shows a rear view of fingerprint capture and storage unit of the first embodiment of the sample capture and storage unit wherein a frangible element of the rear cover is broken to show access to a pin.

The rear shutter 30 comprises a body 33, a first elongate member 34 and a second elongate member 35. The first elongate member 34 has a proximal end 34a which extends from the body 33 and a distal end 34b. This allows some flexibility of the distal end 34b with respect to the body 33. A first pin 31 is located at the distal end 34b of the first elongate member 34 and extends from the inside face 30a of the rear shutter 30. The first elongate member 34 comprises two parallel beams which act to increase flexibility of the distal end 34b of the elongate member 34 with respect to the body.

Figure 11:
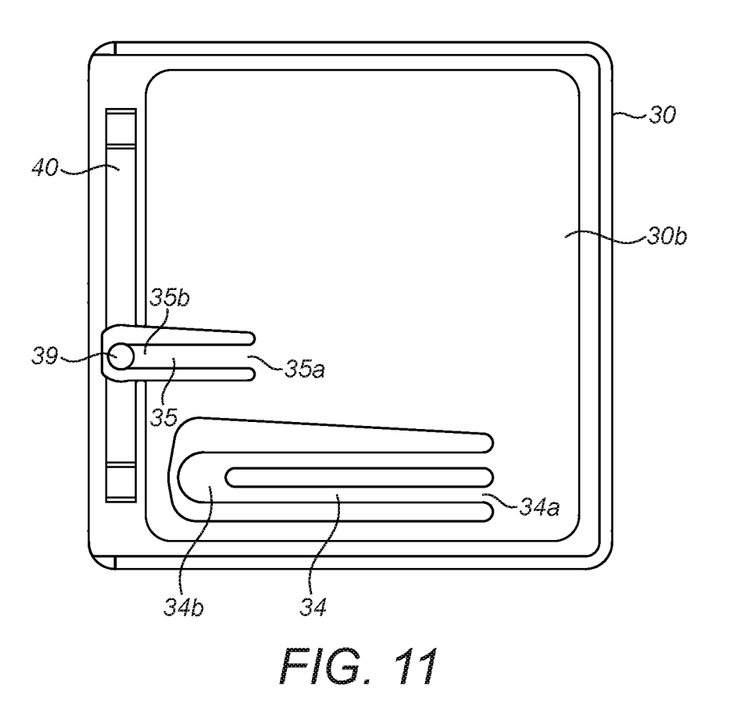
FIG. 11 shows an outside view of a rear shutter of the first embodiment of the sample capture and storage unit with a cover of the rear shutter removed.

The second elongate member 35 has a proximal end 35a which extends from the body 33 and a distal end 35b. This allows some flexibility of the distal end 35b with respect to the body 33. A second pin 32 is located at the distal end 35b of the second elongate member 35 and extends from the inside face 30a of the rear shutter 30. A third pin 39 is located at the distal end 35b of the second elongate member 35 and extends from the outside face 30b of the rear shutter 30 (as shown in FIG. 11).

Figure 10:
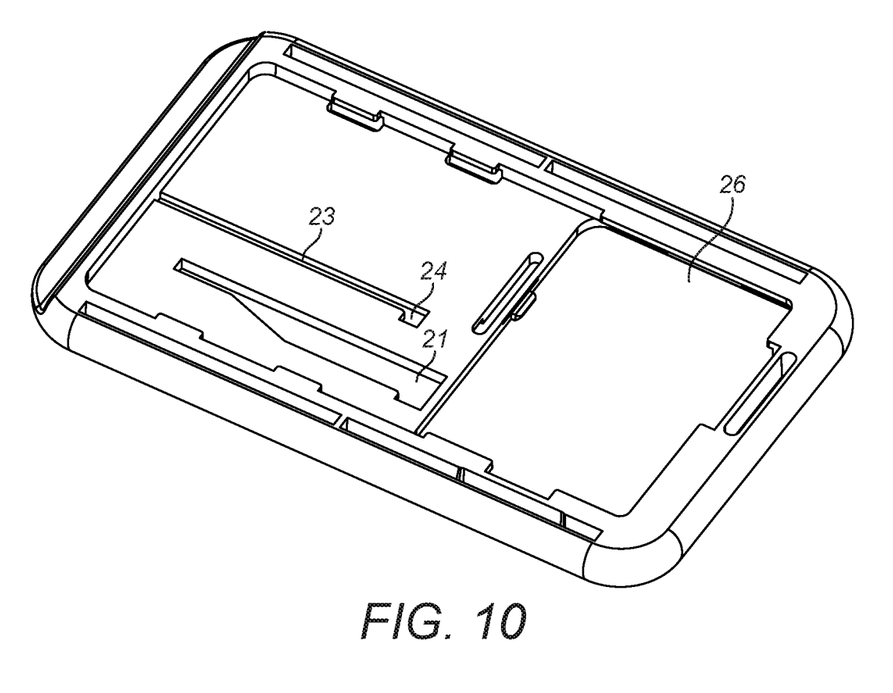
FIG. 10 shows a bottom side of the frame of the first embodiment of the sample capture and storage unit.

The first pin 31 has a diamond-shaped cross-section, the second pin 32 has a rectangular-shaped cross-section and the third pin 39 has a circular cross-section. The first pin 31 is longer than the second pin 32. The first pin 31 is arranged to protrude through an aperture 21 in the frame 20 (best shown in FIG. 10) and is retained within the bifurcated channel arrangement 11 of the front shutter 10. The aperture 21 is shaped so that it does not act to prevent movement of the pin within the bifurcated channel arrangement 11 of the front shutter 10.

Figure 3:
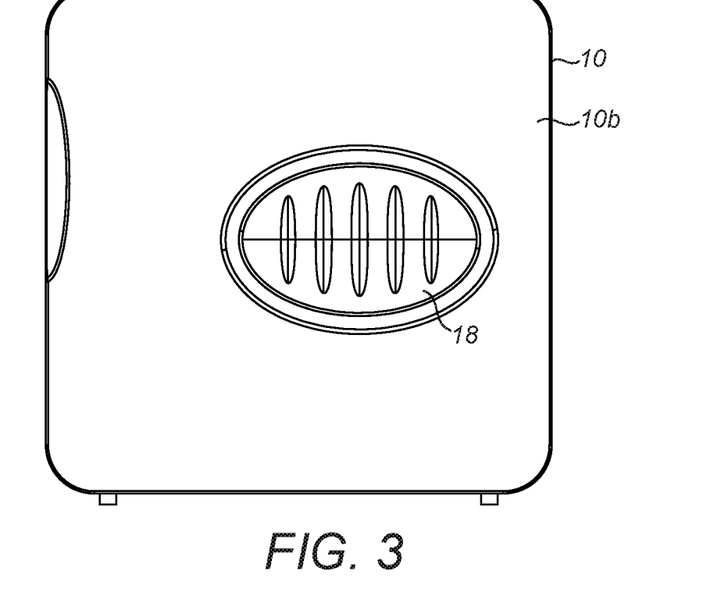
FIG. 3 shows an outside of a front shutter of the first embodiment of the sample capture and storage unit.

In the first closed position of the front shutter (FIG. 1, FIG. 3), the first pin 31 is located at or towards an end of the primary channel 15 that is furthest from the common channel 13.

Sliding the front shutter 10 from the first closed position into the first open position causes the first pin 31 to pass along the primary channel 15 into the common channel 13. The protrusion 18 in the primary channel provides resistance which must be overcome in order for the front shutter to move from the first closed position into the first open position. The protrusion has a smooth cross-sectional shape which results in a gradual reduction in width of the primary channel 15. Resistance must be overcome in order for the diamond-shaped first pin 31 to pass the protrusion. The purpose of the resistance is to avoid the front shutter moving unintentionally from the first closed position into the first open position. For example, it avoids the front shutter moving from the first closed position to the first open position merely under gravity which might otherwise happen in the event that the sample capture and transport unit 1 is positioned so that the common channel 13 is below the primary channel 15.

In the first open position of the front shutter 10, the first pin 31 is located at or towards an end of the common channel 13 which is furthest from the primary and secondary channels 15, 16.

Sliding the front shutter, again using the thumb grip 18, from the first open position into the second closed position causes the first pin 31 to pass along the common channel 13 into the secondary channel 16. The front shutter 10 is prevented from returning to the first closed position since the first pin is prevented from travelling into the primary channel 15 by virtue of one or more kinks in the primary channel 15 and/or the secondary channel 16. Alternatively, or in addition, the first pin 31 may be prevented from travelling into the primary channel 15 by virtue of a biasing effect on the first pin 31. In the specific embodiment illustrated herein, an axis of the primary channel 15 diverges away from an axis of the common channel 13 as the primary channel 15 approaches the common channel 13. Conversely, an axis of the secondary channel 16 converges towards the axis of the common channel 13 as the secondary channel 16 approaches the common channel 13.

In this way, as the first pin moves down the primary channel 15 towards the common channel 13, it is increasingly biased transversely to the axis of the primary channel 15. Once the first pin 31 moves into the common channel 13 it falls back to an unbiased transverse position.

As the first pin 31 moves down the common channel 13 towards the secondary channel 16, the first pin 31 is unbiased and, as such, as it moves axially there is no transverse biasing which would be necessary to cause it to pass into the primary channel 15. This results in the first pin 31 passing into the secondary channel 16. As the first pin moves down the secondary channel 16 away from the common channel 13, the axis of the secondary channel 16 diverges from the axis of the common channel which means that the first pin 31 is increasingly transversely biased.

In the second closed position, the first pin 31 is received into a first detent 17 which is located at or towards an end of the secondary channel 16 furthest from the common channel 13. Receipt of the first pin 31 into the first detent 17 is caused by the transverse biasing on the pin. Once the pin moves transversely to be received into the first detent 17, the transverse biasing is much reduced or eliminated.

In the second closed position, with the first pin 31 received into the first detent 17, the diamond shaped cross-sectional shape of the first pin 31 combined with the step-shaped first detent 17 and the absence of biasing on the first pin 31 mean that the first pin 31 is not removable from the first detent 17. As such, the front shutter 10 is prevented from moving from the second closed position into the first open position.

In specific circumstances the rear shutter 30 is movable with respect to the frame from a closed position in which the rear surface of the substrate is covered by the rear shutter 30 to an open position in which the rear surface of the substrate is exposed for analysis of the appearance of the skin-print through the transparent substrate.

The frame 20 comprises an elongate groove 23 including a second detent 24. In the closed position of the rear shutter 30 the second pin 32 of the rear shutter is retained in the second detent 24.

The rear shutter 30 comprises a cover having a frangible element 35 positioned such that, in the closed position of the rear shutter 30, the frangible element 35 is proximate to the second detent 24 in the frame 20 such that the third pin 39 is accessible only by breaking, removing or otherwise irreversibly damaging the frangible element 35. As such, the frangible element 35 provides evidence of whether or not the third pin 39 has been accessed. In the event that the frangible element 35 is damaged there is evidence that the third pin 39 is accessible and, as such, there can be no certainty that the substrate is uncontaminated. The frangible element 35 therefore acts as a tamper evident feature of the sample capture and transport unit 1.

Breaking the frangible element 35 allows access to the third pin 39. Once accessible, the third pin 39 can be moved transversely which causes the distal end 35b of the second elongate member 35 also to move transversely. This has the further effect of causing the second pin 32 to move transversely which allows the second pin 32 to be removed from the second detent 24. Consequently, the second pin 32 may slide along the groove 23 such that the rear shutter 30 is openable with respect to the frame 20 into the open position of the rear shutter 30. Beneath the frangible element 35 there is an elongate slot 40 perpendicular to the elongate grove 23. An elongate actuator may be received into the elongate slot 40 once the tamper evident feature is triggered. Movement of the elongate actuator in a direction parallel to the direction of the elongate groove 23 causes the second pin 32 to slide along the elongate groove 23 in the sliding direction.

Since the first pin 31 is fixedly attached to the rear shutter 30 and, in the second closed position of the front shutter 10, the first pin 31 is received into the first detent 17 which prevents movement of the first pin 31 relative to the front shutter 10, so the rear shutter 30 is fixedly connected to the front shutter 10.

As a consequence, in the event that the second pin 32 is removed from the second detent 24 and passes along the groove 23 in order that the rear shutter 30 opens, at the same time the front shutter 10 also opens by moving from the second closed position to a second open position.

Use of the sample capture and transport unit 1 will now be described.

The sample capture and transport unit 1 is supplied with the front shutter 10 in the first closed position and the rear shutter in the closed position.

In order to receive a skin-print, the front shutter 10 is manually moved with respect to the frame 20 from the first closed position into the first open position. A user may effect this movement by sliding the front shutter 10 using the thumb grip 18. In the first open position, the front surface of the substrate contained within the substrate receiving portion 26 of the frame 20 is accessible through the open front shutter 10. A skin-print may then be received onto the front surface of the substrate.

Once the skin-print impression has been left on the front surface of the substrate, the front shutter 10 may be moved with respect to the frame 20 into the second closed position. The second closed position prevents the front shutter 10 from being re-opened by sliding the front shutter 10 with respect to the frame 20. This is because, as previously explained, the diamond-shaped first pin 31 is received into the first detent 17 and is retained in the first detent 17 which results in the front shutter 10 being fixed with respect to the rear shutter 30 to which the first pin 31 is fixedly attached.

In order to open the front shutter 10 and rear shutter 30 for analysis of the skin-print, a frangible element 35 is broken in order to access the third pin 39. Accordingly, the third pin 39 may be moved transversely in order that the second pin 32 may be released from the second detent 24 so as to be free to move along the groove 23. Moving of the rear shutter 30 into the open position may be effected by an elongate actuator which is received into the elongate slot 40 located behind the frangible element 35 once the frangible element 35 has been triggered. Having released the second pin 32 from the second detent 24, when the rear shutter 30 is moved with respect to the frame 20 the rear shutter 30 moves to the open position as the second pin 32 moves along the groove 23.

Simultaneously, since the front shutter 10 is fixedly attached to the rear shutter 30 by virtue of the first pin 31 (which is fixedly attached to the rear shutter 30 and is retained in the first detent 17), so when the rear shutter 30 moves from the closed position to the open position also the front shutter 10 moves from the second closed position to the second open position.

With both the front shutter 10 and the rear shutter 30 open, both sides of the substrate are exposed for analysis of the skin-print impression left on the front surface of the substrate.

It may be that the breaking of the frangible element 35 is configured to be performed by an analysis machine. The analysis machine may receive the sample capture and transport unit 1, automatically break the frangible element 35 and move the third pin 39 transversely such that the second pin 32 is released from the second detent 24 so as the second pin 32 can slide along the groove 23. It may then slide the rear shutter 30 into the open position since the second pin 32 is no longer prevented from sliding along the groove 23. In moving the rear shutter 30 into the open position in this manner, simultaneously, the front shutter 10 moves into the second open position.

The analysis machine may then analyse the skin-print either from the front surface of the substrate or from the back surface of the substrate or both. This analysis may take many forms. One option is that an image (i.e. an optical image) of the skin-print is taken through the rear surface of the transparent substrate for analysis. This analysis may include, for example, comparison of the image with a database of images of skin-prints to determine the identity of the skin-print. Also, chemical analysis of the skin-print may be undertaken on the front surface of the substrate.

It is not essential to the invention that the sample capture and transport unit 1 comprises both front and rear shutters. For many applications, only a single shutter may be necessary. This may be the case where the substrate is not transparent, meaning that a conventional transmission optical image cannot be obtained through the back surface of the substrate.

In the event that access to the rear of the substrate is not required, a simpler sample capture and transport unit than that of the first embodiment may suffice. In such an alternative embodiment, it may be that the bifurcated channel arrangement is retained but, in the absence of a rear shutter, the groove 23 and second detent 24 are not present in the frame. Instead, an alternative frangible element may be provided in order, when broken, to provide access to the first pin 31 to enable it to be transversely biased out of the first detent 17 such that the first pin 31 can move along the secondary channel 16 to enable the front shutter 10 to move from the second closed position to the first open position.

As the skilled person would readily understand, the particular arrangements of channels, grooves and detents are not essential to the invention. In its broadest form the invention, which is defined by the appended claims, requires a shutter which is manually openable once then, once closed, is locked closed and can only be re-opened by breaking of a frangible member or otherwise damaging the sample capture and transport unit in a manner which is immediately apparent from its appearance.

Also within the scope of the disclosure is a machine for analysing a skin-print received on a sample-capture substrate located in a substrate chamber of a sample capture and transport unit as described above.

The machine may comprise means for engaging with the sample capture and transport unit in order to overcome the effect of the guiding element which prevents movement from the first open configuration to the first closed configuration.

The machine may be further configured to break the tamper evident feature and disable the non-return feature thereby to access the sample-capture substrate.

The machine may comprise a slot into which the sample capture and transport unit is receivable such that access to the sample-capture substrate is obtained in the manner described above and such that the sample-capture substrate is aligned for analysis of the substrate within the machine.

The invention claimed is:

1. A sample capture and transport unit for use with a sample-capture substrate, the sample capture and transport unit comprising a housing defining a substrate chamber for containing a sample-capture substrate, the housing comprising at least a first part and a second part which are movable relative to one another
   i) from a first closed configuration in which the substrate chamber is inaccessible;
   ii) to a first open configuration in which access to the substrate chamber is enabled to allow capturing of a skin-print on a sample-capture substrate contained within the substrate chamber; and subsequently
   iii) into a second closed configuration, different from the first closed configuration, in which the substrate chamber is again inaccessible;
   wherein the sample capture and transport unit further comprises a retaining mechanism for retaining the sample capture and transport unit in the second closed configuration wherein the retaining mechanism is disablable to permit movement of the sample capture and transport unit out of the second closed configuration,
   wherein the sample capture and transport unit further comprises a tamper evident feature that prevents access to the retaining mechanism,
   wherein access to the retaining mechanism for disabling the retaining mechanism is available only by triggering the tamper evident feature,
   wherein the retaining mechanism comprises a biasing member and a detent into which the biasing member is received in the second closed position,
   wherein the first part of the housing comprises the biasing member and the second part of the housing comprises the detent,
   wherein the second part of the housing comprises a channel arrangement,
   wherein the biasing member of the first part of the housing comprises a first pin retained within the channel arrangement,
   wherein the channel arrangement comprises a bifurcated channel arrangement having:
     a first part comprising a common channel; and
     a second part comprising a primary channel and a secondary channel, the primary channel and the secondary channel being substantially parallel, and
   wherein:
     in the first closed configuration the pin is located in the primary channel;
     in the first open configuration the pin is located in the common channel; and
     in the second closed configuration the pin is located in the secondary channel.

2. The sample capture and transport unit of claim 1 wherein access to the retaining mechanism for disabling the retaining mechanism is restricted.

3. The sample capture and transport unit of claim 1 further comprising a non-return feature which prevents movement from the first open configuration to the first closed configuration.

4. The sample capture and transport unit of claim 1 further comprising a second open configuration accessible only by disabling the retaining mechanism.

5. The sample capture and transport unit of claim 1 wherein the tamper evident feature comprises a frangible element having an undamaged initial configuration in which the retaining mechanism is inaccessible and a damaged configuration which allows access to the retaining mechanism to allow disabling of the retaining mechanism.

6. The sample capture and transport unit of claim 1 wherein the secondary channel comprises the detent.

7. The sample capture and transport unit of claim 1 wherein the primary channel comprises a protrusion, wherein the protrusion is configured to provide resistance to movement of the pin within the primary channel, said resistance to be overcome in order to move the sample capture and transport unit from the first closed configuration to the first open configuration.

8. The sample capture and transport unit of claim 1 wherein either the first part of the housing comprises a frame and the second part of the housing comprises a front shutter or wherein the second part of the housing comprises a frame and the first part of the housing comprises a front shutter,
wherein the frame comprises the substrate chamber.

9. The sample capture and transport unit of claim 5 further comprising a rear shutter of the housing movable from a closed position to an open position,
wherein in all of:
the first closed configuration of the housing;
the first open configuration of the housing; and
the second closed configuration of the housing,
the rear shutter is configured to be in the closed position.

10. The sample capture and transport unit of claim 9 wherein the rear shutter is configured to move into the open position on movement of the sample capture and transport unit into the second open configuration.

11. The sample capture and transport unit of claim 1 further comprising the sample-capture substrate being located in the substrate chamber.

12. The sample capture and transport unit of claim 11 wherein the sample-capture substrate is of material which permits transmission of electromagnetic radiation.

13. The sample capture and transport unit of claim 12 wherein the sample-capture substrate is of material which permits transmission of visible electromagnetic radiation.

14. The sample capture and transport unit of claim 11 wherein the sample-capture substrate is of metal, preferably aluminium or a metal alloy.

15. The sample capture and transport unit of claim 1 wherein the first and second closed configurations are light-proof.

16. The sample capture and transport unit of claim 1 wherein the skin-print is a fingerprint.

17. A machine for analysing a sample received on a sample-capture substrate located in a substrate chamber of a sample capture and transport unit of claim 1, the machine comprising:
means for engaging with the sample capture and transport unit in order to trigger the tamper evident feature and disable the retaining element which prevents movement from the first open configuration to the first closed configuration.

18. The machine of claim 17 for use with a sample capture and transport unit of claim 1 wherein the machine is configured to trigger the tamper evident feature and disable the retaining element thereby to access the sample-capture substrate.

19. A machine according to claim 17 wherein the machine comprises one or more of:
a fluorescence analyser;
a Raman spectrometer for one or more of ultra-violet, visible or infra-red radiation;
a mass spectrometer; and
a chromatography unit.

20. A method of obtaining a sample at a first location, securing the sample for transport and analysing the sample at a second location using the sample capture and transport unit of claim 1 and a sample-capture substrate contained therein, the method comprising the following steps:
at the first location, moving the sample capture and transport unit from the first closed configuration to the first open configuration;
receiving a sample on the sample-capture substrate located in the substrate chamber;
moving the sample capture and transport unit from the first open configuration to the second closed configuration; and
disabling the retaining mechanism in order to access the sample-capture substrate for analysis.

21. The method of claim 20 further comprising, after the step of moving the sample capture and transport unit from the first open configuration to the second closed configuration, the further step of:
transporting the sample capture and transport unit to the second location to disable the retaining mechanism in order to access the sample-capture substrate for analysis.

22. The method of claim 20 wherein the step of accessing the sample-capture substrate comprises triggering a tamper evident feature in order to disable the retaining mechanism of the sample capture and transport unit.

23. The method of claim 20 wherein the step of disabling the retaining mechanism and accessing the sample-capture substrate for analysis and then analysing the sample-capture substrate is performed by a machine.

* * * * *